CHRYSANTHEMUN PLANT

Original Filed Dec. 11, 1970 3 Sheets-Sheet 1

INVENTOR
SING LING LEE

BY
ATTORNEYS

SING LING LEE

ATTORNEYS

United States Patent Office

Re. 28,304
Reissued Jan. 21, 1975

28,304
CHRYSANTHEMUM PLANT

Sing Ling Lee, Mountain View, Calif., assignor to Yoder Brothers Inc., Barberton, Ohio

Original Plant Patent No. 3,249, dated Aug. 1, 1972, Ser. No. 97,396, Feb. 11, 1970. Application for reissue Apr. 13, 1973, Ser. No. 350,907
Int. Cl. A01h *5/00*
U.S. Cl. Plt.—77 1 Claim

Matter enclosed in heavy brackets [ ] appears in the original plant patent but forms no part of this reissue specification; matter printed in italics indicates the additions made by ressue.

---

The present invention comprises a new and distinct cultivar of chrysanthemum plant *known by the varietal name Jumbo Albatross* which is a sport of the cultivar known in the United States as improved Albatross.

The new cultivar is similar in many respects to Improved Albatross, having the same characteristics of:

1. Flower color.
2. Foliage color.
3. Flowering period.

The new cultivar is distinguished from Improved Albatross by the following characteristics:

1. *3–4* [5–7] days earlier and more uniform response.
2. 1" larger and more tightly incurved flowers.
3. Less twisting and reflexing of petals, which are approximately ⅛" wider.
4. Fewer staminodal petals.
5. Stronger, heavier stems.
6. 1"–3" taller, depending on culture.

and Barberton, Ohio. The new cultivar has been found to retain its distinctive characteristics through successive propagations.

The new cultivar when grown in the vicinity of Mountain View, Calif., has a response period of approximately 8 weeks. The following detailed description is based on observations made of both the new and parent cultivars in Barberton, Ohio. It will be understood that the response time, blooming period, color, and total vigor of the new cultivar may vary significantly with varying environmental conditions such as temperature, day length and light intensity. Suggested flowering of the new cultivar in the northern and western United States is from April through May and Nov. 1 through Nov. 15; in coastal California, April through November.

Figure 1:
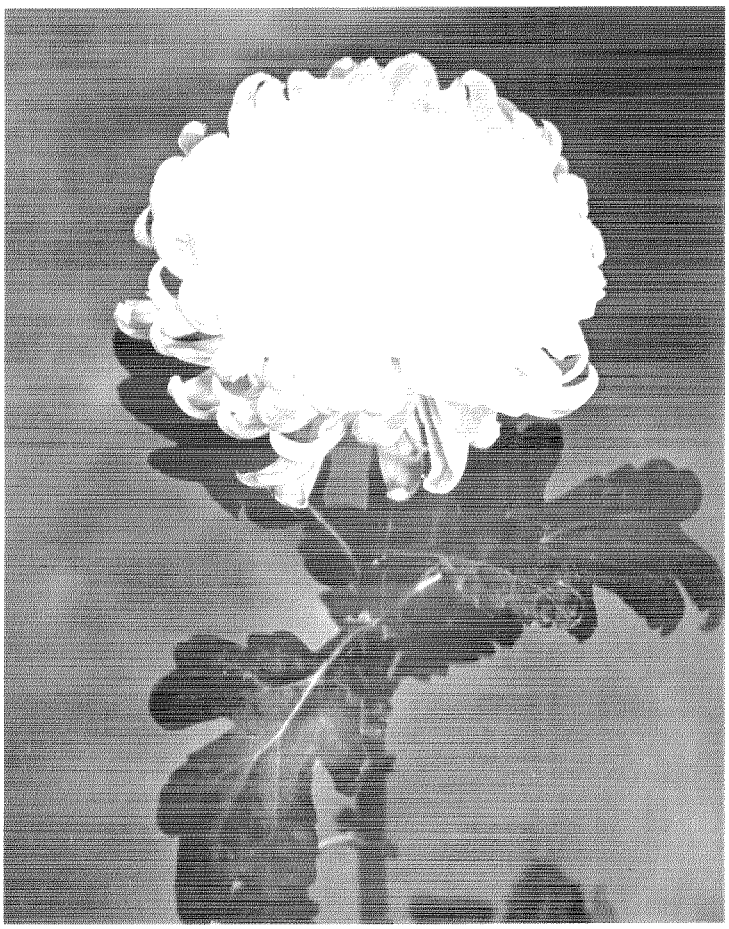
Figure 2:
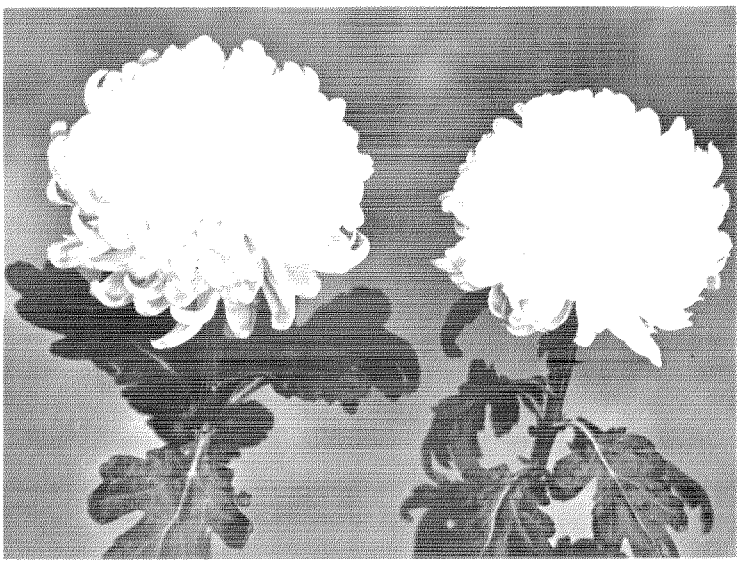
Figure 3:
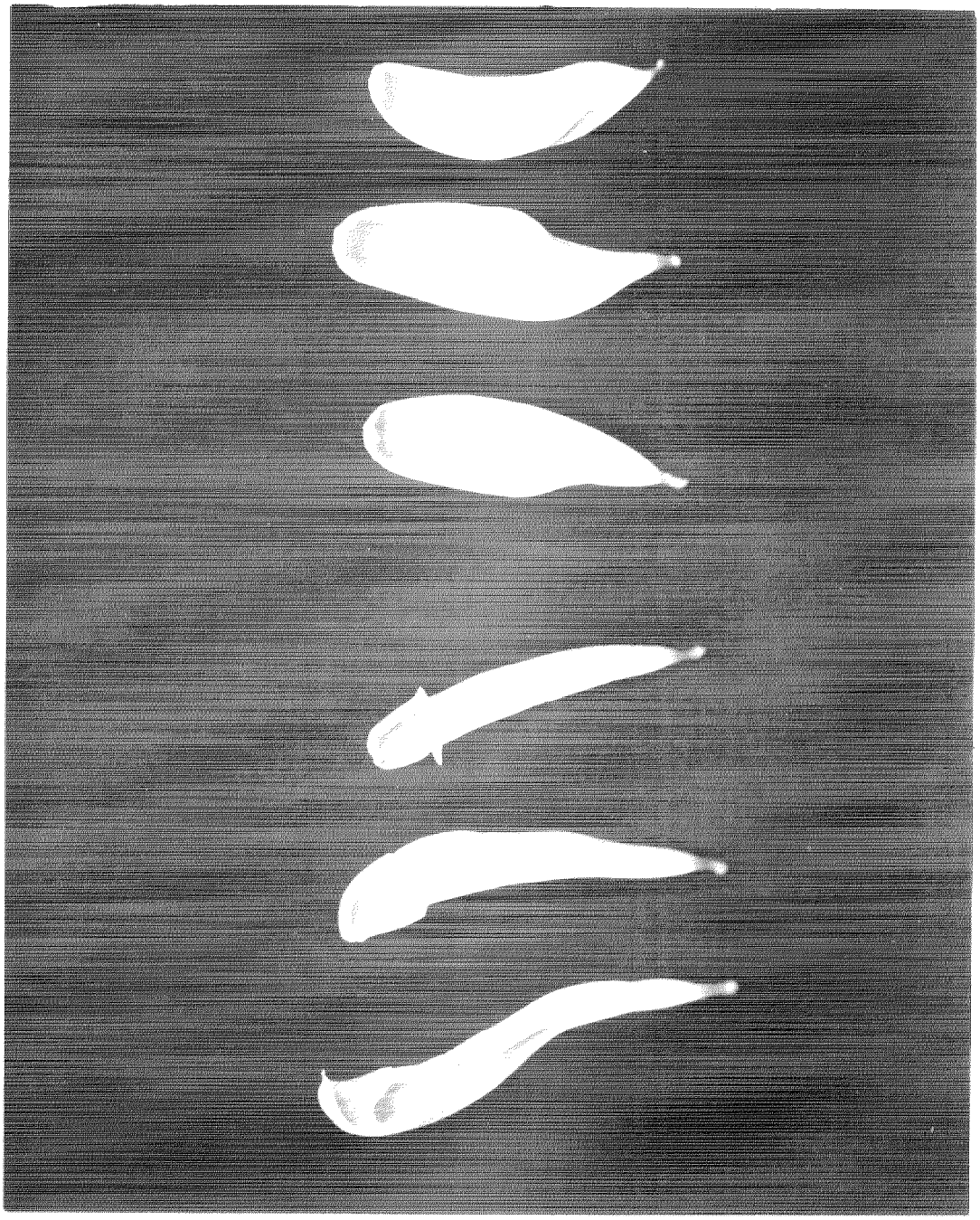

The accompanying drawings show the unique characteristics of the new cultivar, the color being as nearly true as possible with color illustrations of this type. FIG. 1 is an enlarged view of the new cultivar itself . [, and] FIG. 2 is a comparison view with the parent cultivar Improved Albastross, with the latter appearing on the right and the new cultivar on the left. *FIG. 3 is a black and white comparison photograph showing the unique petal form of the new cultivar relative to the cultivar Albatross. The three petals on the left are of the new cultivar, and the three petals on the right are of the cultivar Albatross. The petal form of Albatross is very similar to the petal form of Improved Albatross.*

In the description which follows, color references are to the Munsell Color Book, 1963 edition, and comparisons have been made where differences exist with the parent cultivar Improved Albatross.

Botanical Classification: Chrysanthemum morifolium:

| | Jumbo Albatross | Improved Albatross |
|---|---|---|
| Bloom: | | |
| Size | 5½" | 4½". |
| Fully expanded | 6" | 5". |
| Borne | Singly on disbudded plant | Singly on disbudded plant. |
| Stems | Strong | Strong. |
| Form | Incurve | Semi-incurve. |
| Permanence | 10 days | 10 days. |
| Color: | | |
| Center of flower | Pale yellow, 7.5Y9/4 | |
| Base of petals | White, 5Y9/1 | |
| Inside of p)tals | do | |
| Reverse of petals | do | |
| Tonality from a distance | White | |
| Discoloration | do | |
| Petals: | | |
| Texture—smooth | | |
| Appearance and form.—[Open at base. Broadly keeled, tapering at terminal to an abrupt point.] | *Petals tubular and closed at the base, flaring to a rounded deep keel which tapers to a blunt tip. Most petals have a finger-like or pointed protuberance(s) which arise on the side of the petals near the opening of the tubed base.* | *Open at base, broadly keeled and tapering at terminal of the petal to a blunt tip.* |

7. Foliage broader lobed with less serration.
8. Superior flower form and form retention.
9. Superior grade performance.
10. *A unique petal form, with the petals tubular and closed at the base and flaring to a rounded deep keel which tapers to a blunt tip. Most petals have a finger-like or pointed protuberance(s) which arise on the side of the petals near the opening of the tubed base. This unique trait of Jumbo Albatross, when grown at a minimum temperature of 60° F., or above for initiation and development, has never been observed on the cultivar Albatross. It is rarely seen on the cultivars Improved Albatross and #2 Yellow Albatross. Similar tubular petals have occasionally been observed on Improved Yellow Albatross, but the protuberances which arise on the side of the petals near the opening of the tube on Jumbo Albatross rarely develop on Improved Yellow Albatross at a 60° F. minimum temperature, or above.*

The new cultivar was selected from a flowering block of the parent variety at Mountain View, Calif., and was asexually reproduced by cuttings at Mountain View, Calif., Arrangement.—Composite, whorled on a single receptacle.
Persistence.—Resist shatter.
Fragrance.—Typical chrysanthemum.

Reproductive organs:
- Stamen, anthers.—None to 5.
- Pollen.—None.
- Arrangement.—Clustered in center of flower, if present.
- Styles.—Present both ray and disc florets.
- Length.—Short.
- Ovaries.—At the base of petal attached to receptacle.

Plant:
- Form.—Herbaceous.
- Growth.—Upright.
- Height.—43".
- Spread.—None.

Foliage:
- Top side.—Dark green, 7.5GY2/4.
- Size.—5¾" long, 3¼" wide.
- Quantity.—Numerous.
- Shape.—Spatulate lobed.

Texture.—Smooth.
Ribs and veins.—Prominent.
Edge.—Moderately indented.
Serration.—Very slight (in Improved Albatross the serration is slight).
Underside.—Light green, 7.5GY4/4.
Stipules.—Small.

As above indicated, an important distinguishing characteristic of the new cultivar when compared with the parent cultivar Improved Albatross is its superior grade performance. This can best be seen by the following table, which shows grade data on flowering of the respective cultivars in greenhouses at Mountain View, Calif. under identical conditions. The grading increment is ½", from a 6" flower size downward. The numbers under the cultivar headings indicate the number of flowers in each size group.

| Size | Jumbo Albatross | Improved Albatross |
|---|---|---|
| 6" | 310 | 0 |
| 5½" | 540 | 56 |
| 5" | 550 | 500 |
| 4½" | 0 | 640 |
| 4" | 0 | 300 |
| Culls | 70 | 150 |

It will thus be seen that of the total number of flowers of the new cultivar, approximately 95 percent were in the 5"–6" size range, whereas in the flowering of the parent cultivar only approximately 33 percent of the flowers were in this 5"–6" size range.

I claim:

1. A new and distinct cultivar of chrysanthemum which is characterized particularly as to its uniqueness when compared to the parent cultivar Improved Albatross by its *3–4* [5–7] days earlier and more uniform response, 1" larger and more tightly incurved flowers, approximately ⅙" wider petals which undergo less twisting and reflexing, *and which are tubular and closed at the base and flare to a rounded deep keel which tapers to a blunt tip, with most petals having a finger-like protuberance(s) which arise on the side of the petals near the opening of the tubed base when the cultivar is grown at a minimum temperature of 60° F., or above for initiation and development;* fewer staminodal petals, stronger heavier stems, 1"–3" taller depending on culture, foliage broader lobed with less serration, its superior flower form and form retention, and its superior grade performance.

No references cited.

ROBERT E. BAGWILL, Primary Examiner

UNITED STATES PATENT OFFICE

CERTIFICATE OF CORRECTION

PATENT NO. : Re. 28,304

DATED : January 21, 1975

INVENTOR(S) : SING LING LEE

It is certified that error appears in the above-identified patent and that said Letters Patent are hereby corrected as shown below:

In Column 1, lines 3-4, "assignor to Yoder Brothers, Inc., Barberton, Ohio" should be deleted.

In Column 1, line 6, "Feb. 11, 1970" should be --Dec. 11, 1970--.

In Column 1, line 18, "improved" should be --Improved--.

Signed and Sealed this

*twelfth* Day of *August 1975*

[SEAL]

*Attest:*

RUTH C. MASON
*Attesting Officer*

C. MARSHALL DANN
*Commissioner of Patents and Trademarks*